(12) United States Patent
Pratt et al.

(10) Patent No.: US 10,786,242 B2
(45) Date of Patent: Sep. 29, 2020

(54) SHAPEABLE PASSER FOR SURGICAL CABLE OR SUTURE (75) Inventors: William R. Pratt, Newbury Park, CA (US); Vineet K. Sarin, Moorpark, CA (US)

(73) Assignee: KINAMED, INC., Camarillo, CA (US)

( * ) Notice: Subject to any disclaimer, the term of this patent is extended or adjusted under 35 U.S.C. 154(b) by 565 days.

(21) Appl. No.: 13/452,570

(22) Filed: Apr. 20, 2012

(65) Prior Publication Data
US 2013/0110134 A1 May 2, 2013

Related U.S. Application Data (60) Provisional application No. 61/477,379, filed on Apr. 20, 2011.

(51) Int. Cl.
*A61B 17/04* (2006.01)
*A61M 25/00* (2006.01)
*A61M 25/09* (2006.01)
*A61M 25/01* (2006.01)

(52) U.S. Cl.
CPC ...... *A61B 17/0482* (2013.01); *A61B 17/0469* (2013.01); *A61B 17/0483* (2013.01); *A61B 2017/0495* (2013.01); *A61M 25/0026* (2013.01); *A61M 25/0102* (2013.01); *A61M 25/09* (2013.01)

(58) Field of Classification Search
CPC ............ A61B 17/0469; A61B 17/0482; A61B 17/0483; A61B 2017/0495; A61M 25/0102; A61M 25/0026; A61M 25/09
USPC .......................... 606/139, 148, 151, 157, 228
See application file for complete search history.

(56) References Cited

U.S. PATENT DOCUMENTS

| | | | | |
|---|---|---|---|---|
| 5,290,284 A | * | 3/1994 | Adair | 606/37 |
| 5,292,305 A | * | 3/1994 | Boudewijn et al. | 604/43 |
| 5,447,152 A | * | 9/1995 | Kohsai | A61M 16/04 128/207.14 |

(Continued)

FOREIGN PATENT DOCUMENTS

| | | |
|---|---|---|
| EP | 0532109 A1 | 3/1993 |
| FR | 2938441 | 5/2010 |
| WO | WO 9321834 | 11/1993 |

OTHER PUBLICATIONS https://www.thefreedictionary.com/passer, definition of term passer, retrieved 2019 (Year: 2019).*

(Continued)

*Primary Examiner* — Julian W Woo
(74) *Attorney, Agent, or Firm* — M.J. Ram and Associates (57) ABSTRACT A shapeable passer for surgical cable or suture is made from a flexible tubular extrusion which includes at least one lumen arranged to receive the leading end of a surgical cable or suture, and at least one lumen arranged to contain a malleable stiffener element. The lumens and stiffener element are arranged parallel to each other and lengthwise along longitudinal axis of the extrusion, such that the malleable stiffener element enables the malleable portion of the passer to be shaped as desired. The leading ends of the lumens are preferably sealed, capped or tipped, while the trailing ends of the lumens arranged to receive the surgical cables or sutures are preferably flared to facilitate manual insertion of the cables or sutures.

39 Claims, 4 Drawing Sheets

(56) References Cited

U.S. PATENT DOCUMENTS

| | | | | |
|---|---|---|---|---|
| 5,523,092 A * | 6/1996 | Hanson | A61F 2/06 | |
| | | | 424/423 | |
| 5,695,479 A * | 12/1997 | Jagpal | A61M 25/0606 | |
| | | | 604/264 | |
| 6,161,543 A * | 12/2000 | Cox | A61B 17/00234 | |
| | | | 128/898 | |
| 2004/0122363 A1* | 6/2004 | Gribbons et al. | 604/103.04 | |
| 2004/0167595 A1* | 8/2004 | Tuominen | A61M 25/0009 | |
| | | | 607/122 | |
| 2006/0142784 A1 | 6/2006 | Kontos | 606/139 | |
| 2007/0017527 A1* | 1/2007 | Totz | A61M 16/04 | |
| | | | 128/207.15 | |
| 2007/0208252 A1* | 9/2007 | Makower | 600/424 | |
| 2008/0177217 A1* | 7/2008 | Polaschegg | A61K 31/549 | |
| | | | 604/6.16 | |
| 2008/0245374 A1* | 10/2008 | Agnew | 128/887 | |
| 2009/0131980 A1* | 5/2009 | Wiesman | A61B 17/1146 | |
| | | | 606/228 | |
| 2009/0199848 A1* | 8/2009 | Sharratt | A61M 31/00 | |
| | | | 128/200.14 | |
| 2010/0185172 A1* | 7/2010 | Fabro | A61B 1/00078 | |
| | | | 604/500 | |
| 2010/0298644 A1* | 11/2010 | Kleene | A61B 1/2676 | |
| | | | 600/188 | |
| 2011/0238169 A1* | 9/2011 | Jenson | A61F 2/2445 | |
| | | | 623/2.36 | |
| 2011/0282318 A1* | 11/2011 | Crank | A61M 5/30 | |
| | | | 604/500 | |
| 2012/0265055 A1* | 10/2012 | Melsheimer | A61M 25/0041 | |
| | | | 600/424 | |
| 2012/0265221 A1* | 10/2012 | Saliman | A61B 17/062 | |
| | | | 606/144 | |

OTHER PUBLICATIONS

PCT Notification of the International Search Report and the Written Opinion of the International Searching Authority, dated Jul. 9, 2012; for International Application No. PCT/US2012/034558.

* cited by examiner

SHAPEABLE PASSER FOR SURGICAL CABLE OR SUTURE

RELATED APPLICATIONS

This application claims the benefit of provisional patent application No. 61/477,379 to W. Pratt et al., filed Apr. 20, 2011.

BACKGROUND OF THE INVENTION

Field of the Invention

This invention relates generally to surgical cables or sutures, and more particularly to techniques used to assist in the manipulation of such devices during surgery.

Description of the Related Art

Many products are known which serve to hold human body tissues and bones in a desired relationship or position, to aid in their healing when injured or diseased. One such product is the surgical cable, which is wrapped around one or more tissues and/or bones as needed. For example, a surgical cable can be wrapped around the fragments of a fractured bone, such that a compressive force is applied which aids in the healing of the bone. Such a cable is described, for example, in U.S. Pat. No. 6,589,246 to Hack et al. Another product which is commonly used to join tissues together is monofilament suture.

Cables and sutures of this sort must be threaded around and/or through anatomical structures. This requires the leading end of the cable or suture to be manipulated by the surgeon, which can be extremely challenging when working in tightly confined spaces such as those near highly delicate areas such as the spinal column. This task may be made easier if the cable or suture is such that it inherently maintains its shape once bent, as metallic wires or some metallic cables do. However, polymer surgical cables, such as those used for cerclage in orthopedic surgery, for wiring techniques in spinal surgery, for sternum closure in cardiac surgery, as well as for soft tissue applications, do not inherently maintain their shape once bent, due to their flexible and elastic nature; the same is true of monofilament suture. Although instruments exist to provide a pathway for passing cables or sutures in general surgical environments, they are typically bulky, not minimally invasive, poorly suited for constrained environments such as the spinal canal, and are too rigid to be shaped or reshaped during surgery to provide optimal access through and/or around anatomical structures.

One technique employed to make it easier to manipulate a surgical cable or suture involves swaging a needle onto one or both ends of the cable or suture; one such example using a cable is described in U.S. Pat. No. 5,456,722 to McLead et al. The rigidity of the needle simplifies the task of threading it, and its cable, through a confined space. However, this approach can be problematic, especially when employed with a cable that features an inner core encapsulated in a braided outer jacket. To keep the cable components encapsulated within the jacket, the needle would need to be swaged onto the inner core element. Unfortunately, the diameter of the portion of the needle overlapping the core would necessarily be larger than that of the core, thereby complicating the installation of the outer jacket and possibly rendering the cable unsuitable for some applications. A needle might alternatively be swaged onto the cable over the outer jacket; however, this could risk damage to the jacket and unacceptably increase the effective outer diameter of the cable construct. Moreover the swaged needle may not be easily modified in surgery and its geometry may not allow for its use in many applications.

SUMMARY OF THE INVENTION

A 'passer' is presented which, when affixed to the end of a surgical cable or suture, may be shaped, formed, or bent intraoperatively, thereby facilitating the manipulation of the attached cable around and/or through anatomical or implant structures.

The present shapeable passer for surgical cable is made from a flexible tubular extrusion which includes at least one lumen arranged to receive the leading end of a surgical cable, and at least one lumen arranged to contain a malleable stiffener element, typically a metal wire. The lumens are arranged parallel to each other and lengthwise along the long axis of the extrusion, such that the malleable stiffener wire enables the malleable portion of the passer to be shaped as desired. The leading ends of the lumens are preferably sealed, capped or tipped, while the trailing ends of the lumens arranged to receive the surgical cables are preferably flared to facilitate manual insertion of the cables. Numerous shapeable passer variations and implementation options are described herein.

These and other features, aspects, and advantages of the present invention will become better understood with reference to the following description and claims.

BRIEF DESCRIPTION OF THE DRAWINGS

The attached diagrams illustrate several preferred embodiments of the present shapeable passer. The invention is not limited to the precise embodiments or relative sizing scales shown therein.

DETAILED DESCRIPTION OF THE INVENTION

The present shapeable passer (or simply "passer") is a malleable, tubular extrusion that can be intra-operatively shaped, formed, or bent for optimal passage around or through anatomical or implant structures. The extrusion includes at least two lumens; in use, surgical cable or suture ends are temporarily inserted into one or more lumens, and one or more malleable stiffener elements are contained within respective additional lumens, such that the portion of the combined assembly containing the malleable stiffener element may be shaped and passed as desired. The passer preferably adds little additional bulk to the cable or suture ends, and is minimally invasive due to its shape and footprint. The passer is made of a material that is biocompatible, sterilizeable by techniques that are recognized by the medical industry, tissue-friendly, has a low manufacturing cost, and is preferably disposed of after a single use, thus avoiding hazards and challenges associated with disease transmission and re-sterilization.

Note that, by way of example, the discussion below discusses the use of the present passer with surgical cables; however, it is understood that the passer may also be used, in the same manner, with suture. Also note that, while the following discussion refers to one or more malleable stiffener wires, it is understood that the stiffener elements employed within the passer may comprise components other than wires.

The passer is typically used in the following manner. The passer's lumens have leading and trailing ends. First, one end of a surgical cable—typically a polymer surgical cable—is inserted into the trailing end of a lumen. Typically, the cable continues to be fed into the lumen's trailing end until it is fully inserted into the lumen, such that the leading end of the cable abuts, or rests in close proximity to, the leading tip of the passer. The passer is typically at least several inches in length. Next, the leading end of the passer, with the cable end inserted within it, is formed, bent, or shaped as desired; the desired shape is maintained due to the presence of the passer's malleable stiffener wire. Then the passer (with cable end inserted within it) is threaded around or through anatomical or implant structures as needed. Once the passer is passed around or through the desired structure, it is removed, leaving the cable end exposed and available for the next desired step of a surgical procedure. Thus, installing the present passer on a surgical cable and shaping it as desired enables the cable to be passed, hooked, or directed through or around structures such as bones, soft tissues, and implants, or guided through passages such as bone tunnels or the spinal canal.

Figures 1A, 1B, 1D:
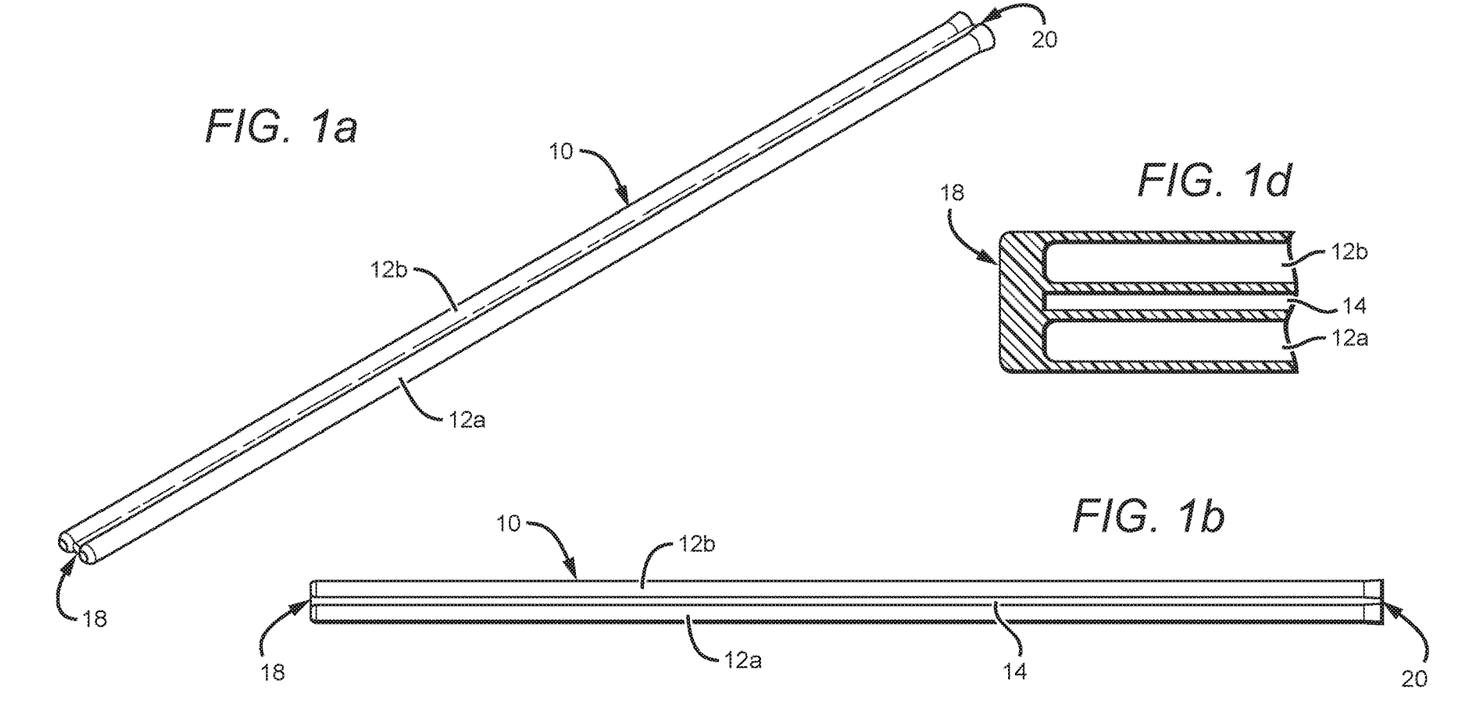
FIGS. 1a, 1b and 1c are oblique, top and side views, respectively, of a shapeable passer in accordance with the present invention.
FIGS. 1d and 1e are detailed and cross-sectional views, respectively, of the leading end of a shapeable passer in accordance with the present invention.
Figure 1C:
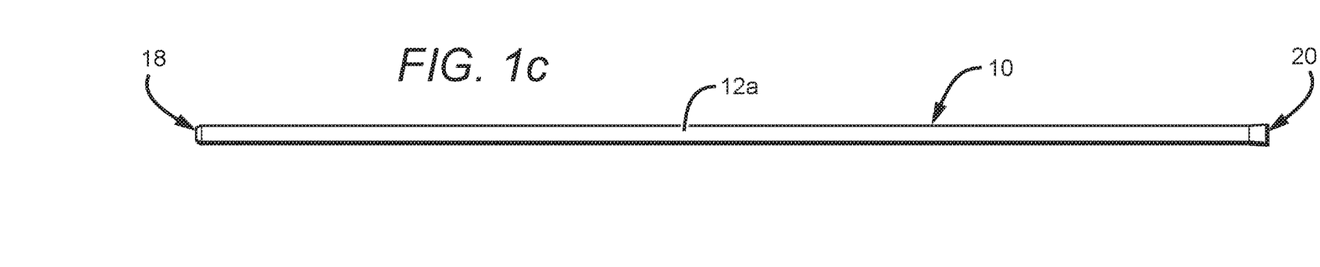
Figure 1E:
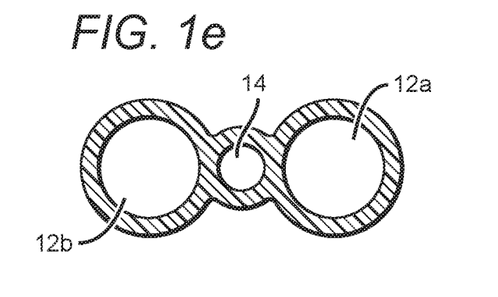

Oblique, top and side views of one possible embodiment of the present shapeable passer are shown in FIGS. 1a, 1b and 1c, respectively; in addition, a detailed view of the leading end of the passer is shown in FIG. 1d, and a cross-section of the extrusion is shown in FIG. 1e. The passer comprises a flexible tubular extrusion 10, which includes at least one lumen (12a, 12b) arranged to receive the leading end of a surgical cable, and at least one malleable stiffener wire which would typically be contained within its own lumen 14. The lumens 12a, 12b, 14 are arranged parallel to each other and lengthwise along the long axis of the extrusion. When so arranged, a passer bent into a desired shape will remain in that shape due to the presence of the malleable stiffener wire. Lumens 12a, 12b are preferably sized to conveniently receive the end of a surgical cable, and lumen(s) 14 is sized to encase a malleable stiffener wire.

The material used for the stiffener wire may be chosen based in part on the passer's desired stiffness. For example, a suitable material might be annealed stainless steel or surgical grade malleable titanium, a less malleable material such as cobalt-chrome, or another biocompatible material or alloy as needed. The diameter or cross-sectional area of the stiffener wire will also affect the stiffness of the wire, with an increased cross-sectional area resulting in a stiffer wire; thus, this parameter might also be varied as needed to obtain a desired stiffness.

Note that the stiffener wire might be arranged such that its properties change along its length, to make it selectively more bendable in certain zones, for example. This might be accomplished by, for example, heat treating, crimping, placing holes in, tapering, flattening, or notching the wire near the tip so that a tighter bend can be formed. Also note that it is not essential that the wire be round, or a single strand wire. For example, the stiffener wire could be non-round, or a ribbon, which could help prevent the wire from toggling or clocking inside the passer when the passer is twisted. The stiffener wire might also be a small diameter braided cable.

Figure 1F:
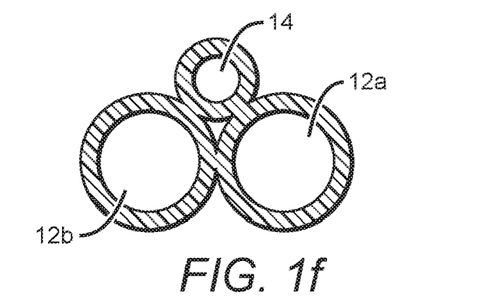
FIGS. 1f, 1g and 1h are cross-sectional views of alternative embodiments of the leading end of a shapeable passer in accordance with the present invention.

The leading end 18 of the extrusion, and thus the leading ends of lumens 12a, 12b, 14 may be sealed, capped, tipped, and/or rounded as needed. The trailing ends 20 of lumens 12a, 12b may be selectively flared to facilitate manual insertion of the cable ends. In cross section, the arrangement of the lumens may be in a row (as shown in FIGS. 1a-1e), preferably with stiffener wire lumen 14 positioned symmetrically between lumens 12a and 12b. One possible alternate footprint is provided if the lumens are arranged in a triangular array as shown in FIG. 1f.

Figure 1G:
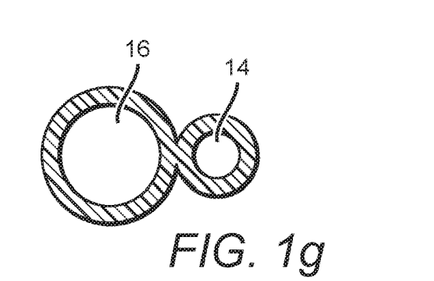
Figure 1H:
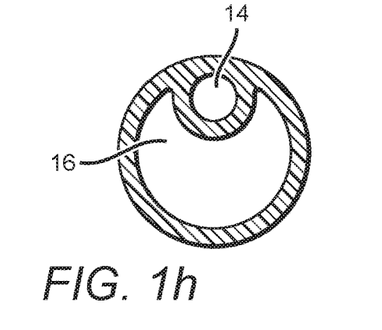

Other possibilities are shown in FIGS. 1g and 1h. Here, the passer would consist of just 2 lumens—one larger lumen 16 sized and shaped to receive two surgical cable ends, and one lumen 14 for the stiffener wire. In general, it may be desirable to arrange the lumens in a configuration that minimizes the passer's frontal cross-sectional footprint, and thereby facilitate the passage of the passer through a patient's tissue.

A passer in accordance with the present invention could be pre-assembled at the manufacturer's site; that is, with the leading ends of the surgical cable(s) fully inserted into the trailing end of the passer prior to packaging and sterilization, such that the assembly (of cable and passer) is presented to the user as a single unit. Thus the cable could be delivered to the surgical field in sterile condition with the passer already installed over the leading ends of the cable. Or, if not pre-assembled in this manner, the passer and cable could be provided as separate items, requiring the surgeon to fully insert the leading cable ends into the trailing end of the passer at the time of surgery. If not pre-assembled, the passer could even be independently manipulated into position, and the leading cable ends then inserted into the open lumens at the trailing end of the device. Yet another possibility would be to provide the passer without cables, which would then be supplied by and inserted by the user.

Similarly, the passer could be provided with a malleable stiffener wire pre-installed into at least one of its lumens. Alternatively, the passer could be provided without a stiffener wire; a stiffener wire or guide wire having desired characteristics would then be supplied and inserted by the user.

Figure 2A:
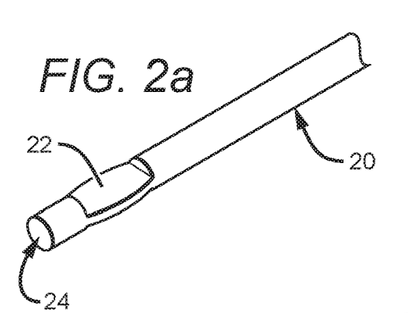
FIGS. 2a, 2b and 2c are oblique, top and side views, respectively, of a malleable stiffener wire as might be used with a shapeable passer in accordance with the present invention.
Figure 2B:
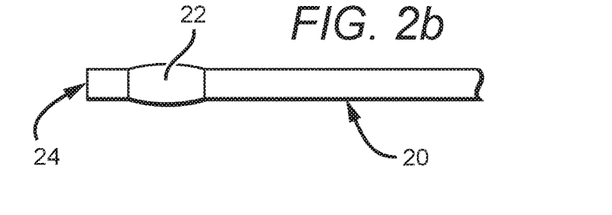
Figure 2C:
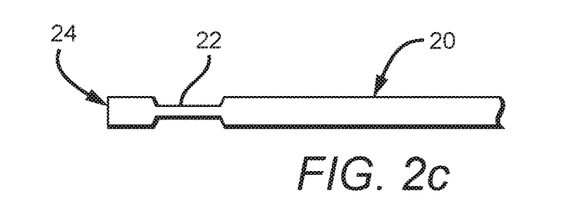

Oblique, top and side views of a preferred embodiment of a malleable stiffener wire 20 are shown in FIGS. 2a, 2b and 2c, respectively. The wire may include an upset feature 22 at its leading end 24 (the end intended to be installed near the leading tip of the passer). This feature enhances the interference fit between the wire and extrusion, mitigating the tendency of the wire to migrate inside the lumen as the passer is manipulated. Malleable stiffener wire(s) 20 would typically be fixed in place within its lumen, in which case the leading end of its lumen would be sealed, capped or tipped.

Alternatively, the passer can be arranged such that the malleable stiffener wire is free to slide within its lumen and used as a guide-wire; in such an embodiment, the lumen intended for the guide-wire would be uncapped. In one possible use for such an arrangement, the tubular extrusion is made to slide freely over a guide-wire which that has been positioned by the surgeon in an advantageous anatomical trajectory. Such an embodiment causes the cable ends to follow the path of the guide-wire as it is fed.

Figures 2D, 2E:
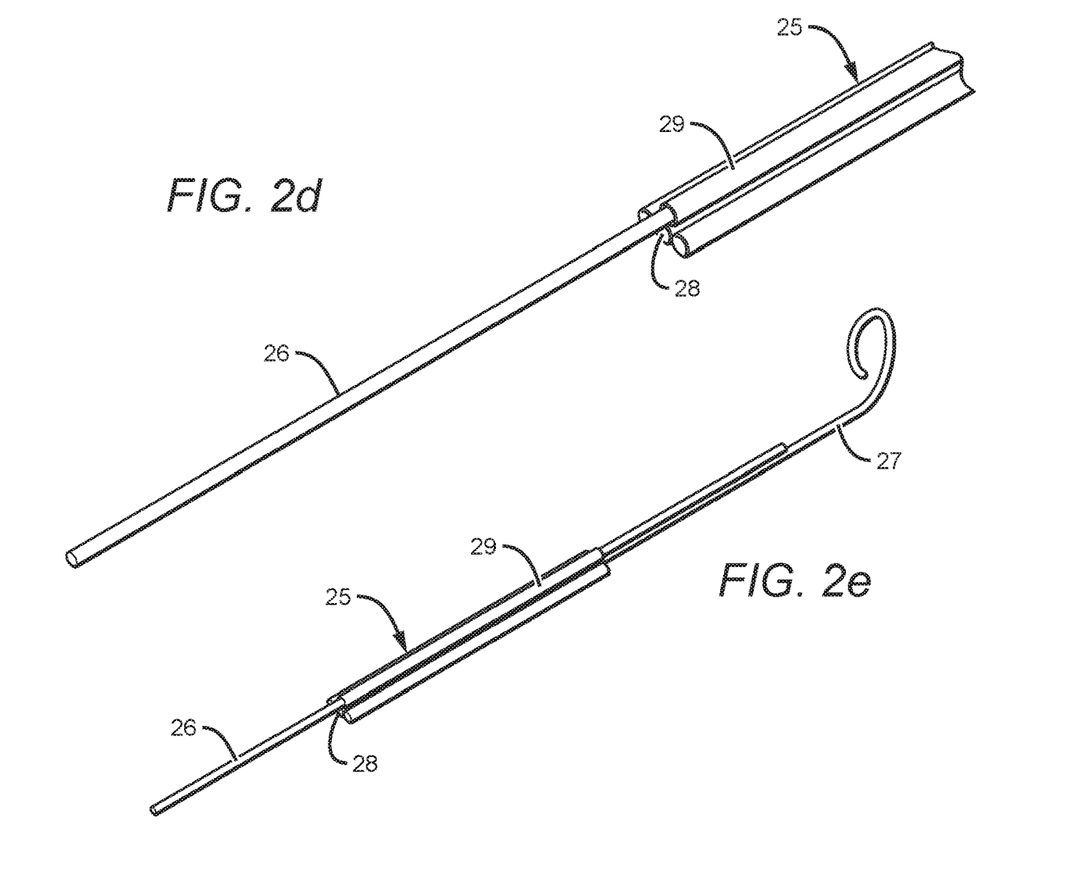
FIGS. 2d and 2e depict a guide-wire and pusher wire arrangement as might be used with a shapeable passer in accordance with the present invention.

Alternatively, an auxiliary wire or coil could be fixed within yet another lumen, and be utilized to push the passer along a guide-wire; this option is illustrated in FIGS. 2d and 2e. The passer 25 slides along the guide-wire 26, and can be propelled by a hand-held pusher wire 27—which in this example has a curled end for grasping. The lumen 28 for the pusher wire is capped, as are the two empty lumens that would accommodate the cable strands, whereas the lumen 29 for the guide-wire is open at both ends. The pusher may be arranged such that the pusher wire is removable from the extrusion, so that it can be independently retracted. In use, the guide wire 26 is first inserted around the anatomical structure, with the ends exposed and accessible. Then the passer 25 is threaded onto the guide-wire, and the cable ends inserted into the passer. Next, the pusher wire 27 is inserted into the remaining lumen until it hits the capped end, at which point it imparts an axial force on the passer, and the passer and cable strands are propelled along the guide-wire and around the anatomical structure until they can be seized on the other side.

Though a passer as described herein could be used with any type of surgical cable, it is particularly well-suited for use with polymer surgical cable. The extrusion preferably comprises surgical-grade polyurethane, with the wall thickness of the lumens suitably on the order of 0.005". Other materials known for their utility in medical tubing applications may also be considered. The diameter of each lumen is sized based on the diameter of the cable or stiffener wire for which it is intended. The extrusion itself may be made from a transparent material to allow the surgeon to visualize the cable(s) embedded within. Alternatively, the extrusion may be made from an opaque material to facilitate viewing of the passer in the presence of blood or other contaminants that are known to inhibit visualization during surgery.

In another possible embodiment, the passer may be made steerable; such a feature might be particularly advantageous in situations of confined access, such as in the cervical spine. A steerable passer could be made, for example, from a multi-durometer extrusion and/or composite materials, with mechanical elements that can effect a curl at the leading end of the passer when actuated by a user, such as a mechanical linkage. Such an embodiment might be comprised of both re-useable and disposable components.

The present shapeable passer might include a lumen capable of receiving a light-carrying filament, to enable illumination of the passer's length and leading end, thereby helping to illuminate the pathway and increase the visibility of the passer's leading end. Another lumen could contain a light-carrying filament to allow for direct visualization of the tissue that the passer is encountering during its passage through the anatomic structure(s). The light-carrying filaments might be, for example, one or more fiber optic filaments or cables. The light-carrying filament may be pre-assembled within the extrusion, or the lumen may remain empty for later insertion of the light-carrying filament(s).

Figure 3:
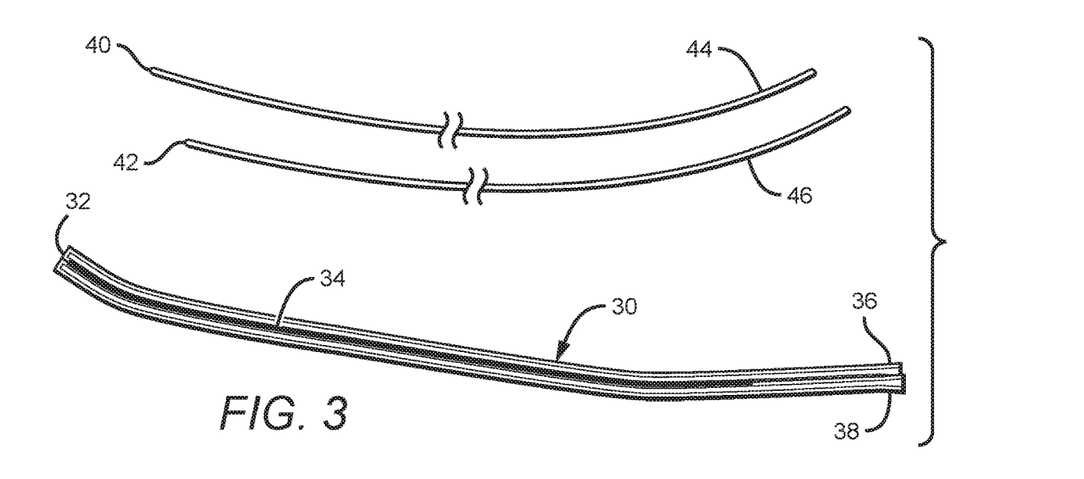
FIG. 3 illustrates a passer and surgical cables prior to insertion of the cable ends into the passer.
Figure 4:
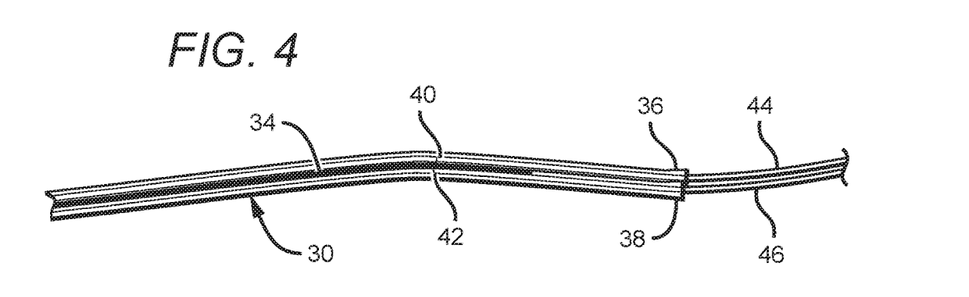
FIG. 4 illustrates a passer and surgical cables with the cable ends partially inserted into the passer.

The present passer is illustrated further in FIGS. 3-6. FIG. 3 illustrates the separate components before they are put into use during surgery. The embodiment shown includes an extrusion 30 having a capped end 32, and which includes one lumen containing a malleable stiffener wire 34 and two lumens having flared ends 36, 38. These two lumens would be sized to receive the ends 40, 42 of surgical cables 44, 46. Then, in FIG. 4, cable ends 40, 42 are partially inserted into the flared ends 36, 38 of their respective lumens.

Figure 5:
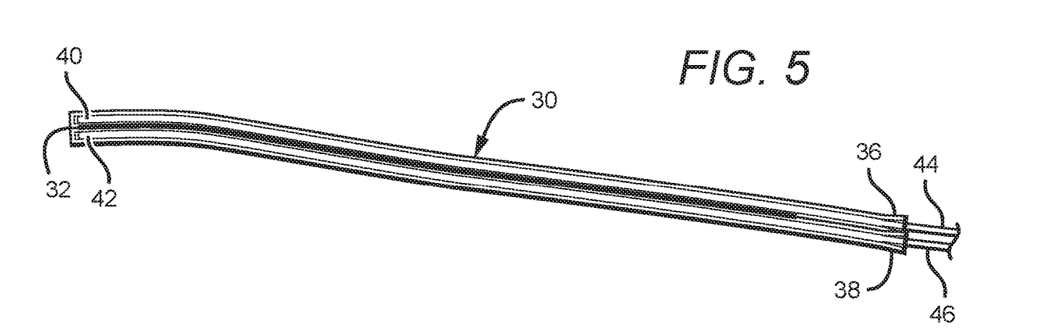
FIG. 5 illustrates a passer and surgical cables with the cable ends fully inserted into the passer.

In FIG. 5, cable ends 40, 42 have been fully inserted into flared ends 36, 38, such that they abut the capped end 32 at the leading tip of the passer. As noted above, the friction between the cable ends and the interior walls of their respective lumens keeps the cables within the extrusion and prevent disengagement.

Figure 6:
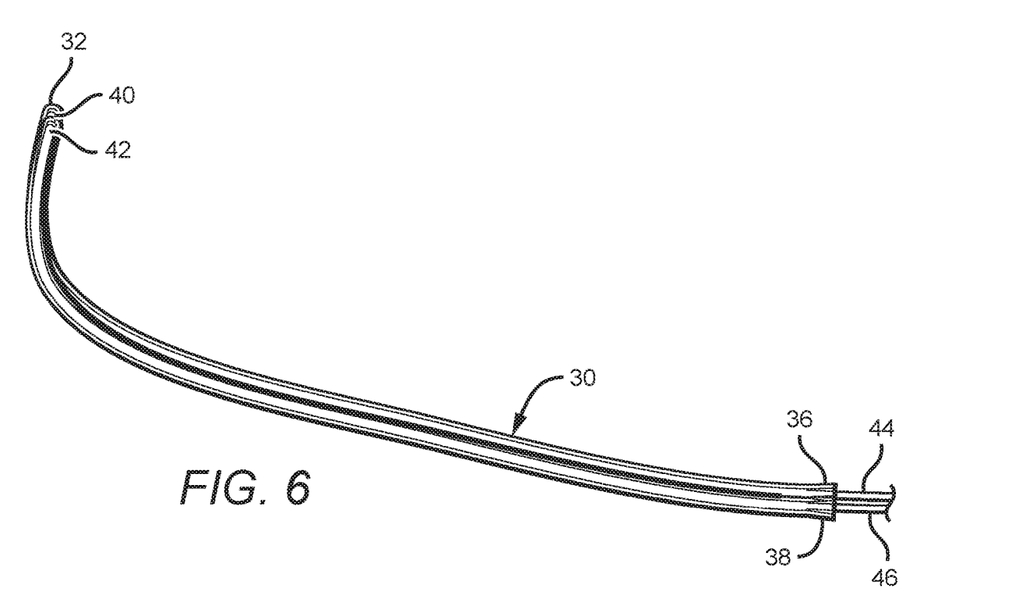
FIG. 6 illustrates a passer and surgical cables with the cable ends fully inserted into the passer, with the passer's leading end bent into a desired shape.

Typically, the surgeon will bend the passer into an advantageous shape to assist in navigating the cable to a desired position, such that the cable can be passed around or through anatomical structures while exposing the anatomy to minimal hazard and protecting the leading ends of the cable. This is illustrated in FIG. 6. Once the cable/passer assembly is positioned where the passer's leading end can be grasped, such as with forceps, the cable/passer assembly is pulled around and clear of the subject tissue, with the remainder of the cable strands following behind. At this point, the passer may be removed from the cable and the installation of the cable continued. A nominal amount of pulling force would typically be needed to remove the passer from the cable ends. The disposable passer may then be discarded.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

We claim:

1. A shapeable passer, comprising:
   at least one surgical cable or suture, each of said at least one surgical cable or suture having a leading end and a trailing end;
   one or more malleable stiffener elements, each of said malleable stiffener elements characterized in that:
      said malleable stiffener element can be intraoperatively shaped into any of multiple possible positions by manually applying a bending force, and
      said malleable stiffener element retains the shape into which it has been manually bent when said bending force is removed; and
   a flexible tubular extrusion, comprising:
      first and second lumens each having a leading end and a trailing end and arranged such that the leading end of at least one surgical cable or suture can be inserted into or withdrawn from said first and second lumens; and
      a third lumen separate and distinct from all other of said extrusion's lumens, said third lumen having a leading end an a trailing end and containing at least one of said malleable stiffener elements such that at least a portion of said passer is malleable, wherein said first and second lumens are arranged parallel to each other and lengthwise along a longitudinal axis of said extrusion and wherein said third lumen is arranged between said first and second lumens, such that the malleable portion of said passer can be intraoperatively shaped into any of multiple possible positions by manually bending said malleable portion, said shape maintained due to the presence of the one or more malleable stiffener elements;
   wherein the leading end of said third lumen is sealed, capped or tipped; and wherein said trailing ends of said first and second lumens are open and flared to facilitate manual insertion of the leading end of said surgical cable or suture.

2. The passer of claim 1, wherein each of said first and second lumens is sized and shaped to receive the leading end of one surgical cables or sutures.

3. The passer of claim 1, wherein said at least one malleable stiffener element is fixed in place within said third lumen.

4. The passer of claim 1, wherein said at least one malleable stiffener elements is free to slide within their respective lumens, wherein said trailing end of said third lumen is uncapped.

5. The passer of claim 4, further comprising an additional lumen and an auxiliary wire or coil within said additional lumen, said additional lumen being arranged such that said auxiliary wire or coil can be utilized by a user to slide the passer along said at least one malleable stiffener element.

6. The passer of claim 1, wherein said leading ends of said first and second lumens are is sealed, capped or tipped.

7. The passer of claim 1, wherein said passer is sterilizable and disposable.

8. The passer of claim 1, wherein said at least one surgical cable or suture is a polymer surgical cable.

9. The passer of claim 1, wherein said at least one surgical cable or suture is a suture.

10. The passer of claim 1, wherein said extrusion comprises surgical- grade polyurethane.

11. The passer of claim 1, wherein said one or more stiffener elements are made from surgical grade stainless steel, titanium, or cobalt-chrome.

12. The passer of claim 1, wherein said extrusion is arranged such that, in cross-section, said first, second and third lumens are arranged in a row.

13. The passer of claim 12, wherein said first and second lumens are positioned symmetrically on either side of said third lumen.

14. The passer of claim 1, wherein said extrusion is arranged such that, in cross-section, said first, second and third lumens are arranged in a triangular array.

15. The passer of claim 1, wherein said lumens are arranged in a configuration that minimizes said passer's frontal cross-sectional footprint and thereby facilitates the passage of said passer through a patient's tissue.

16. The passer of claim 1, wherein a leading end of said extrusion is sealed and formed into a rounded leading tip.

17. The passer of claim 1, wherein said extrusion is made from a transparent material.

18. The passer of claim 1, wherein said extrusion is made from an opaque material.

19. The passer of claim 1, wherein said extrusion is a multi-durometer extrusion, said passer further comprising mechanical elements which can effect a curl at the leading end of said passer when actuated by a user.

20. The passer of claim 1, wherein said at least one polymer surgical cable or suture is a polymer surgical cable, said polymer surgical cable being pre-installed into at least one of said lumens arranged to receive the leading end of a surgical cable or suture.

21. The passer of claim 1, wherein said at least one surgical cable or suture is a suture, said suture being pre-installed into at least one of said lumens arranged to receive the leading end of a surgical cable or suture.

22. The passer of claim 1, further comprising one or more lumens capable of receiving respective light-carrying filaments.

23. The passer of claim 22, wherein at least one of said light-carrying filaments is arranged to enable illumination of said passer's length and leading end.

24. The passer of claim 22, wherein at least one of said light-carrying filaments is arranged to allow for direct visualization of the passage of said passer through a patient's tissues.

25. The passer of claim 22, wherein at least one of said light-carrying filaments is a fiber optic filament.

26. The passer of claim 1, wherein a leading end of at least one of said one or more malleable stiffener elements is configured to enhance an interference fit between said malleable stiffener element and said extrusion.

27. The passer of claim 1, wherein at least one of said one or more malleable stiffener elements is tapered, flattened, or notched near its leading end so as to enable each malleable stiffener element to be formed into tight bends.

28. The passer of claim 1, wherein at least one of said one or more malleable stiffener elements is non-round or a ribbon, so as to reduce the possibility of said wire toggling or clocking inside the passer when the passer is twisted.

29. The passer of claim 1, wherein at least one of said one or more malleable stiffener elements comprises a metal wire.

30. The passer of claim 1, wherein at least one of said one or more malleable stiffener elements comprises a braided cable.

31. The passer of claim 1, wherein said first and second lumens are arranged such that, when said surgical cable or suture is fully installed within either of said first and second lumen's trailing end, friction between said cable or suture and said lumen inhibit the disengagement of said cable or suture from said lumen.

32. The passer of claim 1, wherein at least one of said lumens is arranged to receive a guide-wire, and another of said lumens is capped at one end and arranged to receive a pusher wire, such that said passer can be pushed along said guide wire using said pusher wire.

33. The passer of claim 32, wherein said lumens arranged to receive a guide-wire are open at both ends.

34. The passer of claim 32, wherein said pusher wire is removable from said flexible tubular extrusion.

35. The passer of claim 32, wherein one end of said pusher wire is curled.

36. A shapeable passer, comprising:
at least one surgical cable or suture, each of said at least one surgical cable or suture having a leading end and a trailing end;
a malleable stiffener wire characterized in that:
said malleable stiffener wire can be intraoperatively shaped into any of multiple possible positions by manually applying a bending force, and
said malleable stiffener wire retains the shape into which it has been manually bent when said bending force is removed; and
a flexible tubular extrusion, comprising:
first and second lumens arranged such that the leading ends of respective surgical cables or sutures can be inserted into or withdrawn from said first and second lumens; and
a third lumen separate and distinct from all other of said extrusion's lumens and containing said malleable stiffener wire which is fixed in place within said third lumen, said malleable stiffener wire when contained within said third lumen rendering at least a portion of said passer malleable,
said first, second and third lumens being arranged parallel to each other and lengthwise along a longitudinal axis of said extrusion, wherein said third lumen is arranged between said first and second lumens, such that the malleable portion of said passer can be intraoperatively shaped into any of multiple possible positions by manually bending said malleable portion, said shape maintained due to the presence of said malleable stiffener wire;

wherein each of said lumens has a leading end and a trailing end, the leading ends of said lumens being sealed, capped or tipped;

the trailing ends of said first and second lumens being open and flared to facilitate manual insertion of the leading ends of said surgical cables into said first and second lumens.

37. The passer of claim 36, wherein said extrusion is arranged such that, in cross-section, said first, second and third lumens are arranged in a row, with said first and second lumens positioned symmetrically on either side of said third lumen.

38. The passer of claim 36, wherein said extrusion is arranged such that, in cross-section, said first, second and third lumens are arranged in a triangular array.

39. The passer of claim 36, wherein said lumens are arranged in a configuration that minimizes said passer's frontal cross-sectional footprint and thereby facilitates the passage of said passer through a patient's tissue.

* * * * *